United States Patent
Suleiman et al.

(10) Patent No.: US 10,995,071 B2
(45) Date of Patent: May 4, 2021

(54) METHOD FOR PRODUCING A POLYMORPHIC FORM OF 3-[5-AMINO-4-(3-CYANOBENZOYL)-PYRAZOL-1-YL]-N-CYCLOPROPYL-4-METHYLBENZAMIDE

(71) Applicant: MEREO BIOPHARMA 1 LIMITED, London (GB)

(72) Inventors: Osama Suleiman, Cambridge (GB); Lucia Romero Perez, Royston (GB); Cornelius Stephan Harlacher, Reinach (CH); Stewart Jones, London (GB)

(73) Assignee: MEREO BIOPHARMA 1 LIMITED, London (GB)

( * ) Notice: Subject to any disclaimer, the term of this patent is extended or adjusted under 35 U.S.C. 154(b) by 150 days.

(21) Appl. No.: 16/317,014

(22) PCT Filed: Jul. 13, 2017

(86) PCT No.: PCT/GB2017/052055
§ 371 (c)(1),
(2) Date: Jan. 10, 2019

(87) PCT Pub. No.: WO2018/011578
PCT Pub. Date: Jan. 18, 2018

(65) Prior Publication Data
US 2019/0315694 A1    Oct. 17, 2019

(30) Foreign Application Priority Data
Jul. 14, 2016    (GB) .................................. 1612238

(51) Int. Cl.
*C07D 231/38* (2006.01)

(52) U.S. Cl.
CPC ........ *C07D 231/38* (2013.01); *C07B 2200/13* (2013.01)

(58) Field of Classification Search
CPC .................................................. C07D 231/38
See application file for complete search history.

(56) References Cited

U.S. PATENT DOCUMENTS

| | | |
|---|---|---|
| 7,863,314 B2 | 1/2011 | Fryszman et al. |
| 8,242,117 B2 | 8/2012 | Fryszman et al. |
| 8,410,160 B2 | 4/2013 | Fryszman et al. |
| 8,580,838 B2 | 11/2013 | Lang et al. |
| 9,339,491 B2 | 5/2016 | Ford |
| 10,603,306 B2 | 3/2020 | Orford et al. |
| 10,617,674 B2 | 4/2020 | Orford et al. |

FOREIGN PATENT DOCUMENTS

| | | |
|---|---|---|
| WO | 1999/057101 A1 | 11/1999 |
| WO | 2005/009973 A1 | 2/2005 |
| WO | 2013/139809 A1 | 9/2013 |

OTHER PUBLICATIONS

Caira, Mino R., "Crystalline Polymorphism of Organic Compounds", Topics in Current Chemistry, Springer, Berlin, DE, vol. 198, Jan. 1, 1998 (Jan. 1, 1998), pp. 163-208.
International Search Report and Written Opinion issued in PCT/GB2017/052055 dated Sep. 6, 2017 (13 pages).
Bernstein, J. "Polymorphism of molecular crystals" Moscow, Nauka, 2007, chapter 7.3.2. Bioavailability pp. 244-250.
Sherry L. Morissette et al.: "High-throughput crystallization: polymorphs, salts, co-crystals and solvates of pharmaceutical solids", Advanced drug delivery reviews, 2004, v. 56, pp. 275-300.
Lian Yu, "Amorphous Pharmaceutical Solids: preparation, characterization and stabilization," Advanced Drug Delivery Reviews 28 (2001) pp. 27-42.

*Primary Examiner* — Matthew P Coughlin
(74) *Attorney, Agent, or Firm* — Wolff IP, a Prof Corp; Jessica Wolff

(57) ABSTRACT

This invention relates to a process for the preparation of Form B of 3-[5-amino-4-(3-cyanobenzoyl)-pyrazol-1-yl]-N-cyclopropyl-4-methylbenzamide. Also disclosed herein is Form B of 3-[5-amino-4-(3-cyanobenzoyl)-pyrazol-1-yl]-N-cyclopropyl-4-methylbenzamide, or pharmaceutical compositions thereof, obtainable by the process described herein.

23 Claims, 8 Drawing Sheets

METHOD FOR PRODUCING A POLYMORPHIC FORM OF 3-[5-AMINO-4-(3-CYANOBENZOYL)-PYRAZOL-1-YL]-N-CYCLOPROPYL-4-METHYLBENZAMIDE

CROSS-REFERENCE TO RELATED APPLICATIONS

The present invention is filed under 35 U.S.C. § 371 as the U.S. national phase of International Patent Application No. PCT/GB2017/052055, filed Jul. 13, 2017, which designated the United States, and which claims priority to Great Britain Patent Application No. 1612238.4, filed Jul. 14, 2016, each of which is hereby incorporated by reference in its entirety.

FIELD

Disclosed herein are methods for selectively producing particular crystal polymorphs of the compound 3-[5-amino-4-(3-cyanobenzoyl)-pyrazol-1-yl]-N-cyclopropyl-4-methylbenzamide.

DESCRIPTION OF RELATED ART

Solids exist in either amorphous or crystalline forms. In the case of crystalline forms, molecules are positioned in 3-dimensional lattice sites. Crystallization of solids from solution is known in the art, for example by mixing the desired compound in an appropriate amount of solvent or mixture of solvents, heating to achieve dissolution, and cooling to precipitate the product.

When a compound recrystallizes from a solution or slurry, it may crystallize with different spatial lattice arrangements, a property referred to as "polymorphism", with the different crystal forms individually being referred to as a "polymorph". Different polymorphic forms of a given substance may also differ from each other with respect to one or more physical properties, such as solubility, true density, crystal shape, compaction behaviour, flow properties, and/or solid state stability.

In the case of a chemical substance that exists in two (or more) polymorphic forms having different thermodynamic stabilities, the more unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability of the different polymorphic forms. However, the metastable form may exhibit sufficient chemical and physical stability under normal storage conditions to permit its use in a commercial form. Furthermore, the metastable form, although less stable than the most thermodynamically stable polymorphic form, may exhibit properties that are more desirable than those of the more stable form, such as better formulative ability, improved dispersability in water, and the like.

It has been discovered that the compound 3-[5-amino-4-(3-cyanobenzoyl)-pyrazol-1-yl]-N-cyclopropyl-4-methylbenzamide exists in a large number of polymorphic forms. Many of these forms are undesirable from the point of view of producing pharmaceutically acceptable compositions. This is for a variety of reasons, including lack of stability, high hygroscopicity, low aqueous solubility and handling difficulty.

SUMMARY OF INVENTION

The presently disclosed crystallization methods allow for selectively controlling the crystallization of polymorphic forms of 3-[5-amino-4-(3-cyanobenzoyl)-pyrazol-1-yl]-N-cyclopropyl-4-methylbenzamide. Specifically, the present invention involves a method for the production of a particular polymorphic form of 3-[5-amino-4-(3-cyanobenzoyl)-pyrazol-1-yl]-N-cyclopropyl-4-methylbenzamide hereinafter designated Form B.

Form B, is a crystalline anhydrous form with a melting point of about 216° C., it is non-hygroscopic.

Recrystallization of 3-[5-amino-4-(3-cyanobenzoyl)-pyrazol-1-yl]-N-cyclopropyl-4-methylbenzamide from a range of various solvents leads to mixtures of different polymorphic forms, including solvates, hydrates, anhydrates and the like. If the other polymorphic forms of 3-[5-amino-4-(3-cyanobenzoyl)-pyrazol-1-yl]-N-cyclopropyl-4-methylbenzamide obtained during recrystallisation cannot be converted to Form B, then it must be disposed of, resulting in lost revenue and inefficient production processes.

Form B has particular advantages in terms of pharmaceutical formulation and handling. Form B is particularly advantageous as it in non-hygroscopic, thermodynamically stable, and has a favourable solubility profile, all of which make it easy to formulate, and provide a favourable solubility, hence bioavailability profile. The methods of the present invention produce a free flowing powder which is easy to handle and process to produce pharmaceutical formulations including 3-[5-amino-4-(3-cyanobenzoyl)-pyrazol-1-yl]-N-cyclopropyl-4-methylbenzamide.

To date, there are no simple methods for controlling the crystallization of polymorphic forms of 3-[5-amino-4-(3-cyanobenzoyl)-pyrazol-1-yl]-N-cyclopropyl-4-methylbenzamide. There is thus an urgent and unmet need in the art for efficient methods for selectively controlling the crystallization of polymorphic forms of 3-[5-amino-4-(3-cyanobenzoyl)-pyrazol-1-yl]-N-cyclopropyl-4-methylbenzamide.

It has been found that embodiments disclosed herein satisfy this heretofore unmet need in that they provide a process for selectively controlling the crystallization of polymorphic forms of 3-[5-amino-4-(3-cyanobenzoyl)-pyrazol-1-yl]-N-cyclopropyl-4-methylbenzamide. In particular, the presently claimed methods allow improved control of particle properties, such as particle size, enable improved yields of specific polymorphs and reduce contamination by residual solvents.

In a first aspect, there is provided a process for the preparation of a crystalline polymorph Form B of 3-[5-amino-4-(3-cyanobenzoyl)-pyrazol-1-yl]-N-cyclopropyl-4-methylbenzamide, comprising:

(a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution, wherein the solvent or solvents contain less than about 5 wt % of water relative to the 3-[5-amino-4-(3-cyanobenzoyl)-pyrazol-1-yl]-N-cyclopropyl-4-methylbenzamide starting material;

(b) cooling the solution;

(c) isolating the crystals;

(d) heating the resultant crystals to greater than 75° C. for a period of greater than 1 minute to produce Form B 3-[5-amino-4-(3-cyanobenzoyl)-pyrazol-1-yl]-N-cyclopropyl-4-methylbenzamide.

In a second aspect, there is provided a process for the preparation of a crystalline polymorph Form B of 3-[5- amino-4-(3-cyanobenzoyl)-pyrazol-1-yl]-N-cyclopropyl-4-methylbenzamide, comprising:
  (a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution;
  (b) cooling the solution;
  wherein the temperature of process step (b) does not exceed 100° C.;
  (c) isolating the crystals;
  (d) heating the resultant crystals to greater than 75° C. for a period of greater than 1 minute to produce Form B 3-[5-amino-4-(3-cyanobenzoyl)-pyrazol-1-yl]-N-cyclopropyl-4-methylbenzamide.

In a third aspect, there is provided a process for the preparation of a crystalline polymorph Form B of 3-[5-amino-4-(3-cyanobenzoyl)-pyrazol-1-yl]-N-cyclopropyl-4-methylbenzamide, comprising:
  (a) dissolving 3-[5-amino-4-(3-cyanobenzoyl)-pyrazol-1-yl]-N-cyclopropyl-4-methylbenzamide, at a temperature of 40° C. or greater, preferably 100° C. or greater, in a non-aqueous solvent or mixture of non-aqueous solvents to obtain a solution;
  (b) optionally filtering the solution to substantially remove particles having a largest diameter greater than 100 µm, preferably less than 10 µm;
  (c) cooling the solution to less than 100° C., preferably less than 90° C., but greater than 80° C.;
  (d) seeding the solution with Form B crystals of 3-[5-amino-4-(3-cyanobenzoyl)-pyrazol-1-yl]N-cyclopropyl-4-methylbenzamide;
  (e) optionally cooling the solution further;
  (f) optionally further seeding of the solution with Form B crystals of 3-[5-amino-4-(3-cyanobenzoyl)-pyrazol-1-yl]-N-cyclopropyl-4-methylbenzamide;
  (g) cooling the solution to less than 70° C.
  (h) isolating the crystals of Form B 3-[5-amino-4-(3-cyanobenzoyl)-pyrazol-1-yl]-N-cyclopropyl-4-methylbenzamide.

BRIEF DESCRIPTION OF DRAWINGS

Certain aspects of the embodiments described herein may be more clearly understood by reference to the drawings, which are intended to illustrate, but not limit, the invention, and wherein.

DETAILED DESCRIPTION OF SPECIFIC EMBODIMENTS

The starting material for any aspects of the invention may be any source of 3-[5-amino-4-(3-cyanobenzoyl)-pyrazol-1-yl]-N-cyclopropyl-4-methylbenzamide. For example the starting material for the method of producing Form B according to the present invention may be selected from the group consisting of crude, amorphous, polymorphic (other than pure Form B or including Form B), a mixture of polymorphs of 3-[5-amino-4-(3-cyanobenzoyl)-pyrazol-1-yl]-N-cyclopropyl-4-methylbenzamide, and mixtures thereof. For example, the 3-[5-amino-4-(3-cyanobenzoyl)-pyrazol-1-yl]-N-cyclopropyl-4-methylbenzamide starting material used for preparing Form B according to the disclosed process in WO 2005/009973 (such as Example 161 thereof).

The methods of any of the aspects of the present invention produce pure Form B 3-[5-amino-4-(3-cyanobenzoyl)-pyrazol-1-yl]-N-cyclopropyl-4-methylbenzamide.

As used herein, "pure form B" means crystalline polymorphic Form B having less than 10% by weight of any other polymorphic form of 3-[5-amino-4-(3-cyanobenzoyl)-pyrazol-1-yl]-N-cyclopropyl-4-methylbenzamide, preferably less than 5% by weight, preferably less than 2% by weight, preferably less than 1% by weight, preferably less than 0.5% by weight, preferably less than 0.1% by weight of other polymorphic forms of 3-[5-amino-4-(3-cyanobenzoyl)-pyrazol-1-yl]-N-cyclopropyl-4-methylbenzamide.

The powder XRD patterns and data for polymorphic form B is distinctly different to other polymorphic forms of 3-[5-amino-4-(3-cyanobenzoyl)-pyrazol-1-yl]-N-cyclopropyl-4-methylbenzamide. Form B exhibits an X-ray powder diffraction pattern substantially as given in the table below, having characteristic peaks (expressed in degrees 2θ (+/− 0.2° θ) at one or more of the following positions:

| Angle - 2-Theta ° | Intensity % |
|---|---|
| 9.6 | 12.2 |
| 10.1 | 9.9 |
| 11.4 | 100.0 |
| 13.1 | 5.4 |
| 13.9 | 7.4 |
| 14.8 | 37.3 |
| 15.4 | 16.3 |
| 15.8 | 9.4 |
| 17.0 | 16.2 |
| 17.4 | 29.9 |
| 18.5 | 33.3 |
| 18.8 | 17.9 |
| 19.7 | 14.6 |
| 19.9 | 19.9 |
| 20.5 | 18.0 |
| 21.0 | 27.7 |
| 21.9 | 36.5 |
| 22.9 | 48.5 |
| 23.6 | 47.8 |
| 24.6 | 42.4 |
| 25.7 | 26.8 |

Figure 1:
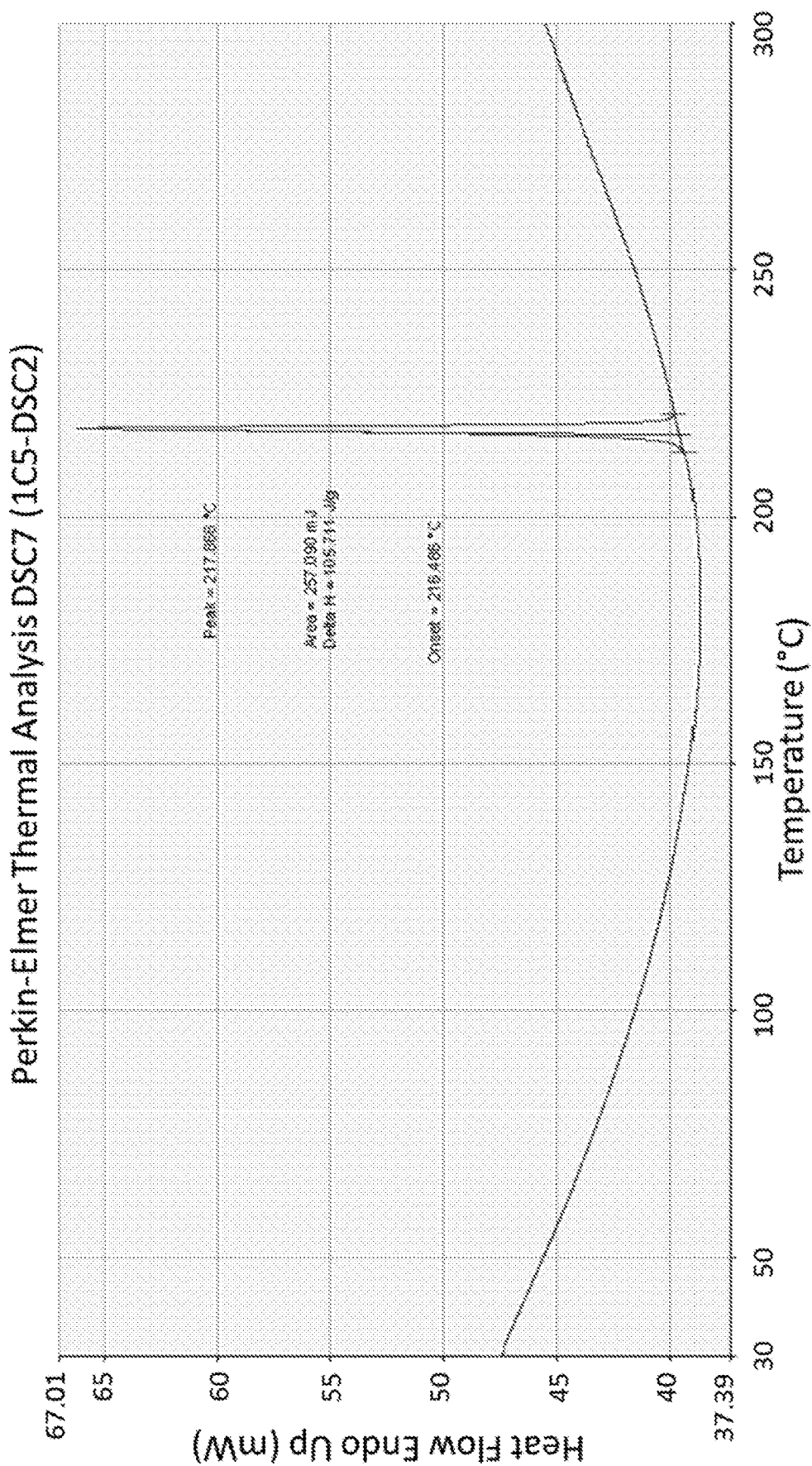
FIG. 1 is a graph of a thermogram obtained by DSC of Form B polymorph of 3-[5-amino-4-(3-cyanobenzoyl)-pyrazol-1-yl]-N-cyclopropyl-4-methylbenzamide.

Form B of 3-[5-amino-4-(3-cyanobenzoyl)-pyrazol-1-yl]-N-cyclopropyl-4-methylbenzamide also exhibits a differential Scanning calorimetry (DSC) thermogram substantially as shown in FIG. 1. This thermogram is characterized by a predominant endotherm peak at about 216° C.

Useful formulations of compositions containing Form B can be prepared in conventional ways. These include preparation as dusts, pellets, solutions, suspensions, emulsions, wettable powders, and the like.

Preferably, in the first aspect of the invention, the temperature of process steps (a) and (b) does not exceed 140° C., preferably does not exceed 100° C., preferably does not exceed 90° C.

Preferably, in the first aspect of the invention, the temperature of process step (d) is greater than 80° C., preferably greater than 85° C., preferably greater than 90° C., preferably greater than 100° C. Preferably, in the first aspect of the invention, the temperature of process step (d) is less than 210° C., preferably less than 180° C., preferably less than 140° C., preferably less than 120° C.

Preferably, in the first aspect of the invention, the temperature of process step (d) is maintained for greater than 5 minutes, preferably greater than 15 minutes, preferably greater than 1 hour, preferably greater than 4 hours. The heating is preferably carried out in an oven.

For example, in the first aspect of the invention, the temperature of process step (d) is greater than 80° C., for greater than 5 minutes, preferably greater than 15 minutes, preferably greater than 1 hour, preferably greater than 4 hours.

Preferably, in the first aspect of the invention, the cooling in step (b) is preferably at a cooling rate of about between 1 and 0.01° C./min, preferably between 0.5 and 0.05° C./min, preferably between 0.2 and 0.08° C./min, preferably at about 0.1° C./min. This helps to prevent or reduce the formation of other polymorphs of 3-[5-amino-4-(3-cyanobenzoyl)-pyrazol-1-yl]-N-cyclopropyl-4-methylbenzamide.

Preferably, in the first aspect of the invention, in the cooling in step (b) the solution is cooled to less than 90° C.

During step (b) of the first or second aspect of the invention, an anti-solvent may be added to encourage precipitation of the desired crystals. Preferred anti-solvents include $C_{1-6}$ ethers and $C_{1-6}$ nitroalkanes, such as t-butyl methyl ether and nitromethane. However, the skilled person will readily be able to select an anti-solvent depending on what solvent is used in the process.

The anti-solvent:solvent ratio is preferably in the range of 0.1:1-1:0.1.

During steps (a) and (b) of the first aspect of the invention, if water is present in greater than about 5% water, relative to the weight of the 3-[5-amino-4-(3-cyanobenzoyl)-pyrazol-1-yl]-N-cyclopropyl-4-methylbenzamide, a hydrate of 3-[5-amino-4-(3-cyanobenzoyl)-pyrazol-1-yl]-N-cyclopropyl-4-methylbenzamide is formed in unacceptable quantities, thereby constituting an impurity.

According to the first aspect of the invention, the term "nonaqueous solvent or mixture of non-aqueous solvents" means one or more solvents selected from the group consisting of $C_{1-6}$ alcohols, $C_{4-10}$ cyclic ethers, $C_{1-6}$ nitriles, $C_{1-6}$ haloalkanes, $C_{1-6}$ ketones, dialkylformamides, dialkyl sulfoxides, $C_{3-10}$ aryls, $C_{5-10}$ alkanes, $C_{1-6}$ alkyl acetate, preferably in the substantial absence of water. Preferred nonaqueous solvents are selected from the group consisting of methanol, ethanol, tetrahydrofuran, acetonitrile, methylene chloride, isopropyl alcohol, acetone, N,N-dimethylformamide (DMF), dimethyl sulfoxide (DMSO), toluene, benzene, n-hexane, ethyl acetate, dichloromethane, chloroform and carbon tetrachloride, preferably in the substantial absence of water. Particularly preferred nonaqueous solvents are selected from the group consisting of ethanol, isopropyl alcohol and isobutanol, preferably in the substantial absence of water.

Preferably, in the second aspect of the invention, the temperature of process step (d) is greater than 80° C., preferably greater than 80° C., preferably greater than 90° C., preferably greater than 100° C. Preferably, in the second aspect of the invention, the temperature of process step (d) is less than 210° C., preferably less than 180° C., preferably less than 140° C.

Preferably, in the second aspect of the invention, the solvent or solvents used in step (a) contain less than about 5 wt % of water relative to the 3-[5-amino-4-(3-cyanobenzoyl)-pyrazol-1-yl]-N-cyclopropyl-4-methylbenzamide starting material.

Preferably, in the second aspect of the invention, the temperature of process step (d) is maintained for greater than 5 minutes, preferably greater than 30 minutes, preferably greater than 1 hour, preferably greater than 4 hours.

For example, in the second aspect of the invention, the temperature of process step (d) is greater than 80° C. for a period of greater than 5 minutes, preferably greater than 30 minutes, preferably greater than 1 hour, preferably greater than 4 hours.

Preferably, in the second aspect of the invention, the cooling in step (b) is preferably at a cooling rate of about between 1 and 0.01° C./min, preferably between 0.5 and 0.05° C./min, preferably between 0.2 and 0.08° C./min, preferably at about 0.1° C./min. This helps to prevent or reduce the formation of other polymorphs of 3-[5-amino-4-(3-cyanobenzoyl)-pyrazol-1-yl]-N-cyclopropyl-4-methylbenzamide. The selection of this cooling rate helps to improve the yield of Form B and the purity of Form B in the crystalline product.

In particular, any of the above numbered aspects of the invention are capable of producing Form B crystals in a purity of greater than 80 wt % of the starting material, usually greater than 90 wt %, preferably greater than 95 wt %, for example, greater than 98 wt %.

According to the second aspect of the invention, the term "nonaqueous solvent or mixture of non-aqueous solvents" means one or more solvents selected from the group consisting of $C_{1-6}$ alcohols, $C_{4-10}$ cyclic ethers, $C_{1-6}$ nitriles, $C_{1-6}$ haloalkanes, $C_{1-6}$ ketones, dialkylformamides, dialkyl sulfoxides, $C_{3-10}$ aryls, $C_{5-10}$ alkanes, petroleum ether, $C_{1-6}$ alkyl acetate, $C_{1-6}$ ether, preferably in the substantial absence of water. Preferred nonaqueous solvents are selected from the group consisting of methanol, ethanol, tetrahydrofuran, acetonitrile, methylene chloride, isopropyl alcohol, acetone, N,N-dimethylformamide (DMF), dimethyl sulfoxide (DMSO), toluene, benzene, n-Hexane, petroleum ether, ethyl acetate, ether, dichloromethane, chloroform and carbon tetrachloride, preferably in the substantial absence of water. Particularly preferred nonaqueous solvents are selected from the group consisting of ethanol, isopropyl alcohol and isobutanol, preferably in the substantial absence of water.

Preferably, in the third aspect of the invention, the solvent or solvents in step (a) contain less than about 5 wt % of water relative to the 3-[5-amino-4-(3-cyanobenzoyl)-pyrazol-1-yl]-N-cyclopropyl-4-methylbenzamide starting material.

The method of the third aspect of the invention is preferably used for large scale production (greater than 5 kg) of material. The Form B seeds are preferably produced by the method according to the first or second aspects of the invention or from previous runs of the method of the third aspect of the invention. Form B crystals are readily characterised and identified by their XRPD spectrum and other methods described herein.

Preferably, the temperature of the solution in step (a) of the third aspect of the invention is between 90° C. and 200° C., preferably between 100° C. and 180° C., preferably between 103° C. and 125° C., preferably about 105° C.

The filtration step (b) of the third aspect of the invention preferably removes particles having a largest diameter of greater than 50 μm, preferably greater than 20 μm, preferably greater than 10 μm, preferably greater than 5 μm, preferably greater than 1 μm. Preferably, the solution is filtered through charcoal.

The cooling step (c) of the third aspect of the invention is preferably to a temperature of greater than 85° C., preferably about 88° C. Preferably this temperature is maintained for at least 1 hour, preferably at least 2 hours, preferably at least 5 hours.

During steps (c) and/or (e) of the third aspect of the invention, an anti-solvent may be added to encourage precipitation of the desired crystals. Preferred anti-solvents include $C_{1-6}$ ethers, such as t-butyl methyl ether. However, the skilled person will readily be able to select an anti-solvent depending on what solvent is used in the process.

Step (d) of the third aspect of the invention is preferably seeded with greater than 0.1 wt % of Form B 3-[5-amino-4-(3-cyanobenzoyl)-pyrazol-1-yl]-N-cyclopropyl-4-methylbenzamide, relative to the weight of the 3-[5-amino-4-(3-cyanobenzoyl)-pyrazol-1-yl]-N-cyclopropyl-4-methylbenzamide dissolved in step (a), preferably greater than 1 wt %, preferably greater than 3 wt %, preferably greater than 4 wt %.

The cooling step (g) of the third aspect of the invention is preferably at a temperature of less than 50° C. but greater than 0° C., preferably less than 30° C., preferably about 20° C. Preferably this temperature is maintained for at least 30 minutes, preferably 1 hour, preferably at least 2 hours, preferably at least 5 hours.

Preferably the solvent is removed in step (h) of the third aspect of the invention by drying between 40-120° C. under vacuum, preferably 60-100° C. under vacuum.

The cooling step (c) of the third aspect of the invention is preferably maintained above 80° C., but less than 100° C. for a period of at least 5 minutes, preferably greater than 30 minutes, preferably greater than 1 hour.

According to the third aspect of the invention, the term "nonaqueous solvent or mixture of non-aqueous solvents" means one or more solvents selected from the group consisting of $C_{1-6}$ alcohols, $C_{4-10}$ cyclic ethers, $C_{1-6}$ nitriles, $C_{1-6}$ haloalkanes, $C_{1-6}$ ketones, dialkylformamides, dialkyl sulfoxides, $C_{3-10}$ aryls, $C_{5-10}$ alkanes, petroleum ether, $C_{1-6}$ alkyl acetate, $C_{1-6}$ ether, preferably in the substantial absence of water. Preferred nonaqueous solvents are selected from the group consisting of methanol, ethanol, tetrahydrofuran, acetonitrile, methylene chloride, isopropyl alcohol, acetone, N,N-dimethylformamide (DMF), dimethyl sulfoxide (DMSO), toluene, benzene, n-Hexane, petroleum ether, ethyl acetate, ether, dichloromethane, chloroform and carbon tetrachloride, preferably in the substantial absence of water. Particularly preferred nonaqueous solvents are selected from the group consisting of isobutanol and n-pentanol, preferably in the substantial absence of water.

Preferably, the concentration of 3-[5-amino-4-(3-cyanobenzoyl)-pyrazol-1-yl]-N-cyclopropyl-4-methylbenzamide in step (a) is such that seeding was more effective at temperatures of greater than 80° C., preferably about 85° C. Preferably seeding was defined as twice 2 wt. % at between 80° C. and 90° C.

For an improved cool down in step (g) of the third aspect of the invention a preferred maximum rate of 0.05° C./min was used. This helps to prevent or reduce the formation of other polymorphs of 3-[5-amino-4-(3-cyanobenzoyl)-pyrazol-1-yl]-N-cyclopropyl-4-methylbenzamide.

The final temperature in step (g) of the third aspect of the invention was most preferably 20° C., as cooling to 0° C. led in some cases to traces of other polymorphs.

A particularly preferred solvent for dissolving 3-[5-amino-4-(3-cyanobenzoyl)-pyrazol-1-yl]-N-cyclopropyl-4-methylbenzamide in step (g) of the third aspect of the invention is n-pentanol. Preferably cooling to 20° C., preferably at a rate of 0.05° C./min was carried out. Thus method produces greater yield and robustness than other solvents.

Preferably the seeding according to any aspect of the invention is carried out by dispersing the seeds in the same solvent as used to dissolve the 3-[5-amino-4-(3-cyanobenzoyl)-pyrazol-1-yl]-N-cyclopropyl-4-methylbenzamide.

Preferably, the isolation of the crystals of the Form B 3-[5-amino-4-(3-cyanobenzoyl)-pyrazol-1-yl]-N-cyclopropyl-4-methylbenzamide according to any aspect of the invention includes washing with the same solvent used to dissolve the 3-[5-amino-4-(3-cyanobenzoyl)-pyrazol-1-yl]-N-cyclopropyl-4-methylbenzamide in the initial step of the method. The washing is preferably carried out using a solvent at a temperature of less than 30° C.

| Temperature | Solvent | Final polymorph | Duration |
|---|---|---|---|
| 80° C. | EtOH | B | 2 days |
| | n-PrOH | B | 2 days |
| | i-PrOH | B | 2 days |
| | i-BuOH | B | 2 days |
| 70° C. | EtOH | B + other polymorphs | 3 days |
| | n-PrOH | B + other polymorphs | 3 days |
| | i-PrOH | No B | 3 days |
| | i-BuOH | No B | 3 days |
| 60° C. | EtOH | No B | 1 day |
| | n-PrOH | No B | 1 day |
| | i-PrOH | No B | 1 day |
| | i-BuOH | No B | 1 day |
| | $DMAC/H_2O = 1/1$ | hydrate | 1 day |
| | $H_2O$ | hydrate | 1 day |

It can be seen that at a temperature of 70° C., conversion to Form B is effected, but with significant contamination by other polymorphs, particularly over longer periods of time. It can also be seen that the hydrate is formed when water is included in the solvent, even at lower temperatures.

According to the third aspect of the invention, it can be seen that at temperature of 80° C., conversion to Form B is effected, without significant contamination.

In all aspects of the invention, as used herein, the term "substantial absence of water" means less than 5 wt %, relative to the 3-[5-amino-4-(3-cyanobenzoyl)-pyrazol-1-yl]-N-cyclopropyl-4-methylbenzamide used in the process, preferably less than 1 wt %, preferably less than 0.5 wt %, preferably less than 0.1 wt %, preferably less than 0.05 wt %, preferably less than 0.001 wt %.

Furthermore, as shown in FIG. 1, Form B also exhibits a Differential Scanning calorimetry (DSC) thermogram which is characterized by a predominant endotherm peak at about 215° C., as measured by Differential Scanning calorimeter at a scan rate of 10° C. per minute.

The methods of the present invention conveniently produce Form B 3-[5-amino-4-(3-cyanobenzoyl)-pyrazol-1-yl] N-cyclopropyl-4-methylbenzamide having a $D_{50}$ particle size of less than 400 µm, preferably less than 300 µm, preferably less than 200 µm.

The methods of the present invention conveniently produce Form B 3-[5-amino-4-(3-cyanobenzoyl)-pyrazol-1-yl]-N-cyclopropyl-4-methylbenzamide having a $D_{10}$ particle size of greater than 10 µm.

The crystals of Form B are isolated by any conventional method known in the art, for example by filtration, centrifugation, etc.

Prior to or during any of the cooling steps according to any of the above numbered aspects of the invention, the amount of the solvent may be reduced, for example, by distillation, to concentrate the solution of the 3-[5-amino-4-(3-cyanobenzoyl)-pyrazol-1-yl]-N-cyclopropyl-4-methylbenzamide.

The invention will now be described further by reference to the following examples, which are intended to illustrate, but not limit, the scope of the appended claims.

Comparative Example 1

Form A Process Description

3-[5-amino-4-(3-cyanobenzoyl)-pyrazol-1-yl]-N-cyclopropyl-4-methylbenzamide was dissolved in ethanol at 75° C. The obtained solution is filtered over a particle filter to a second reactor. After cooling down to IT (Internal Temperature)=40° C. a seed suspension of 3-[5-amino-4-(3-cyanobenzoyl)-pyrazol-1-yl]-N-cyclopropyl-4-methylbenzamide in ethanol is added. The reaction mixture is kept for additional 2 hours at IT=40° C., before starting a slow cooling ramp (0.1 K/min) to IT=−10° C. The suspension is kept for at least 5 hours at IT=−10° C. The product is isolated on a filter dryer. The filter cake is washed over the reactor by using ethanol in 3 portions without stirring. Drying of the wet filter cake is performed in two operational steps. The first step is done in 5 hours at JT (Jacket Temperature)=50° C. and pressure=10-20 mbar. During this step the stirrer is not in use. The second step is done in 5 hours at JT=60° C. and pressure=10-20 mbar. During this step the stirrer is turned on for 1 min and put for 14 minutes on hold. After this period the content of ethanol ≤0.5%-m/m is fulfilled.

1. Raw Material Availability

The process may use seed crystals, but they are not necessary. The seed crystals, where used, are milled (to produce a higher particle surface area).

Example 1

This method is an embodiment of the third aspect of the invention.

3-[5-amino-4-(3-cyanobenzoyl)-pyrazol-1-yl]-N-cyclopropyl-4-methylbenzamide was dissolved in isobutanol at IT 105° C. The obtained solution is filtered over a particle filter to a second reactor. After cooling down to IT=85° C. a seed suspension of Form B 3-[5-amino-4-(3-cyanobenzoyl)-pyrazol-1-yl]-N-cyclopropyl-4-methylbenzamide in isobutanol is added. The obtained suspension is kept for 1 h at IT=85° C. before starting a slow cooling ramp (0.05 K/min) to IT=82° C. At this temperature a second seed suspension of Form B 3-[5-amino-4-(3-cyanobenzoyl)-pyrazol-1-yl]-N-cyclopropyl-4-methylbenzamide in isobutanol is added. IT=82° C. is kept for an additional 1 h, before starting a very slow ramp (<0.04 K/min). The suspension is kept for at least 5 hours at IT=20° C.

Product Form B 3-[5-amino-4-(3-cyanobenzoyl)-pyrazol-1-yl]-N-cyclopropyl-4-methylbenzamide is isolated on a filter dryer. The filter cake is washed over the reactor by using isobutanol in 3 portions without stirring. Drying of the wet filter cake is performed in two operational steps. The first step is done in 5 hours at JT=60° C. and p=10-20 mbar. During this step the stirred is not in use. The second step is done in 10 hours at JT=80° C. and p=10-20 mbar. During this step the stirrer is turned on for 1 min and put for 14 min on hold. After this period the content of isobutanol ≤0.5%-m/m is achieved.

Figure 5A:
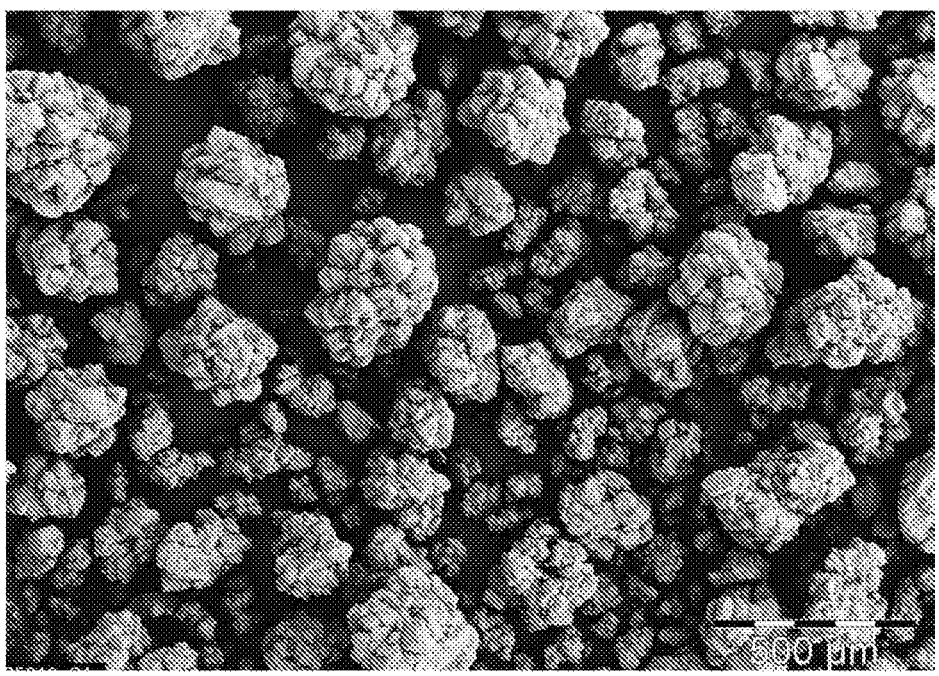
FIGS. 5a and 5b are SEM images of unmilled Form B 3-[5-amino-4-(3-cyanobenzoyl)-pyrazol-1-yl]-N-cyclopropyl-4-methylbenzamide recrystallised by the method of the present invention. This shows spherical aggregates having good flowability characteristics.
Figure 5B:
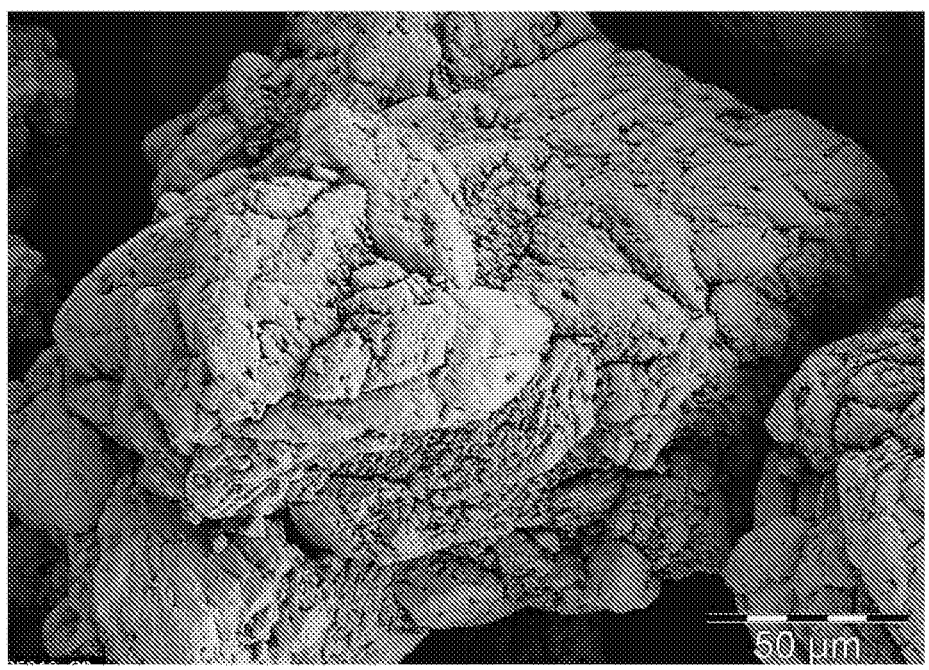

The Form B particles are well flowing aggregates (~250 µm average diameter) of crystals with rather smooth surface, as depicted in the SEM images shown in FIGS. 5a and 5b.

Example 2

This embodiment is an example according to the First and Second aspects of the invention.

3-[5-amino-4-(3-cyanobenzoyl)-pyrazol-1-yl]-N-cyclopropyl-4-methylbenzamide was dissolved in ethanol at 75° C. The obtained solution is filtered over a particle filter to a second reactor. After cooling down to IT (Internal Temperature)=40° C. a seed suspension of 3-[5-amino-4-(3-cyanobenzoyl)-pyrazol-1-yl]-N-cyclopropyl-4-methylbenzamide in ethanol is added. The reaction mixture is kept for additional 2 hours at IT=40° C., before starting a slow cooling ramp (0.1 K/min) to IT=−10° C. The suspension is kept for at least 5 hours at IT=−10° C. The product is isolated on a filter dryer. The filter cake is washed over the reactor by using ethanol in 3 portions without stirring. Drying of the wet filter cake is performed in two operational steps. The first step is done in 5 hours at JT (Jacket Temperature)=50° C. and pressure=10-20 mbar. During this step the stirrer is not in use. The second step is done in 5 hours at JT=60° C. and pressure=10-20 mbar. During this step the stirrer is turned on for 1 min and put for 14 minutes on hold. After this period the content of ethanol ≤0.5%-m/m is fulfilled.

These crystals were converted into Form B by heating them in vacuum dryer at 180° C.

2. Instrument and Methodology Details 2.1 X-Ray Powder Diffraction (XRPD)

2.1.1 Bruker AXS C2 GADDS

X-Ray Powder Diffraction patterns were collected on a Bruker AXS C2 GADDS diffractometer using Cu $K_{alpha}$ radiation (40 kV, 40 mA), automated XYZ stage, laser video microscope for auto-sample positioning and a HiStar 2-dimensional area detector. X-ray optics consists of a single Gabel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2 θ range of 3.2°-29.7°. Typically the sample would be exposed to the X-ray beam for 120 seconds. The software used for data collection was GADDS for XP/2000 4.1.43 and the data were analysed and presented using Diffrac Plus EVA v15.0.0.0.

Samples run under ambient conditions were prepared as flat plate specimens using powder as received without grinding. Approximately 1-2 mg of the sample was lightly pressed on a glass slide to obtain a flat surface.

2.1.2 Bruker AXS D8 Advance

X-Ray Powder Diffraction patterns were collected on a Bruker D8 diffractometer using Cu $K_{alpha}$ radiation (40 kV, 40 mA), 6-28 goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2 θ
Step size: 0.05° 2 θ
Collection time: 0.5 s/step

A short method was used for screening samples. Details of the data collection are:

Angular range: 2 to 31° 2θ
Step size: 0.05° 2θ
Collection time: 0.5 s/step
Non-Ambient Conditions The sample was placed in Anton-Paar TTK 450 chamber at 25° C. The temperature was controlled in-situ through the measurement files: p2853-vt, LRP-1301-39-01.dql, LRP-1301-42-01.dql, LRP-1301-42-02.dql. The sample was heated from 25° C. to 200° C. at 1° C./min. XRPD data were collected from 30° C. to 200° C. every 10° C. Approximately 40 mg of the sample was placed in a Ni-coated sample holder under ambient conditions. The sample was loaded at 25° C.

3. Single Crystal X-Ray Diffraction (SCXRD)

Data were collected on a Rigaku Oxford Diffraction Supernova Dual Source, Cu at Zero, Atlas CCD diffractometer equipped with an Oxford Cryosystems Cobra cooling device. The data was collected using $CuK_{alpha}$ radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

4. Differential Scanning calorimetry (DSC)

5.1 TA Instruments Q2000

DSC data were collected on a TA Instruments Q2000 equipped with a 50 position auto-sampler. The calibration for thermal capacity was carried out using sapphire and the calibration for energy and temperature was carried out using certified indium. Typically 0.5 3 mg of each sample, in a pin-holed aluminium pan, was heated at 10° C./min from 25° C. to 300° C. A purge of dry nitrogen at 50 ml/min was maintained over the sample.

Modulated temperature DSC was carried out using an underlying heating rate of 2° C./min and temperature modulation parameters of ±0.318° C. (amplitude) every 60 seconds (period).

The instrument control software was Advantage for Q Series v2.8.0.394 and Thermal Advantage v5.5.3 and the data were analysed using Universal Analysis v4.5A.

5.2 TA Instruments Discovery DSC

DSC data were collected on a TA Instruments Discovery DSC equipped with a 50 position auto-sampler. The calibration for thermal capacity was carried out using sapphire and the calibration for energy and temperature was carried out using certified indium. Typically 0.5 3 mg of each sample, in a pin-holed aluminium pan, was heated at 10° C./min from 25° C. to 300° C. A purge of dry nitrogen at 50 ml/min was maintained over the sample.

The instrument control and data analysis software was TRIOS v3.2.0.3877.

5. Thermo-Gravimetric Analysis (TGA)

6.1 TA Instruments Q500

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminium DSC pan and heated at 10° C./min from ambient temperature to 350° C. A nitrogen purge at 60 ml/min was maintained over the sample.

The instrument control software was Advantage for Q Series v2.5.0.256 and Thermal Advantage v5.5.3 and the data were analysed using Universal Analysis v4.5A.

6.2 TA Instruments Discovery TGA

TGA data were collected on a TA Instruments Discovery TGA, equipped with a 25 position auto-sampler. The instrument was temperature calibrated using certified alumel and nickel. Typically 5-10 mg of each sample was loaded onto a pre-tared aluminium DSC pan and heated at 10° C./min from ambient temperature to 350° C.

A nitrogen purge at 25 ml/min was maintained over the sample.

The instrument control and data analysis software was TRIOS v3.2.0.3877.

6. Polarised Light Microscopy (PLM)

Samples were studied on a Nikon SMZ1500 polarised light microscope with a digital video camera connected to a DS Camera control unit DS-L2 for image capture. A small amount of each sample was placed on a glass slide, mounted in immersion oil, the individual particles being separated as well as possible. The sample was viewed with appropriate magnification and partially polarised light, coupled to a λ false-colour filter

7. Scanning Electron Microscopy (SEM)

Data were collected on a Phenom Pro Scanning Electron Microscope. A small quantity of sample was mounted onto an aluminium stub using conducting double-sided adhesive tape. A thin layer of gold was applied using a sputter coater (20 mA, 120 s).

8. Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approx 10 mg of sample was used per titration and duplicate determinations were made. Data collection and analysis using Tiamo v2.2.

9. Chemical Purity Determination by HPLC

Purity analysis was performed on an Agilent HP1100 series system equipped with a diode array detector and using ChemStation software vB.04.03 using the method detailed below:

TABLE 1

HPLC method for chemical purity determinations

| Parameter | Value |
|---|---|
| Type of method | Reverse phase with gradient elution |
| Sample Preparation | 0.5 mg/ml in acetonitrile:water 1:1 |
| Column | Supelco Ascentis Express C18, 100 × 4.6 mm, 2.7 μm |
| Column Temperature (° C.) | 25 |
| Injection (μl) | 5 |
| Wavelength, Bandwidth (nm) | 255, 90 |
| Flow Rate (ml/min) | 2 |
| Phase A | 0.1% TFA in water |
| Phase B | 0.085% TFA in acetonitrile |

| Timetable | Time (min) | % Phase A | % Phase B |
|---|---|---|---|
| | 0 | 95 | 5 |
| | 6 | 5 | 95 |
| | 6.2 | 95 | 5 |
| | 8 | 95 | 5 |

Figure 6:
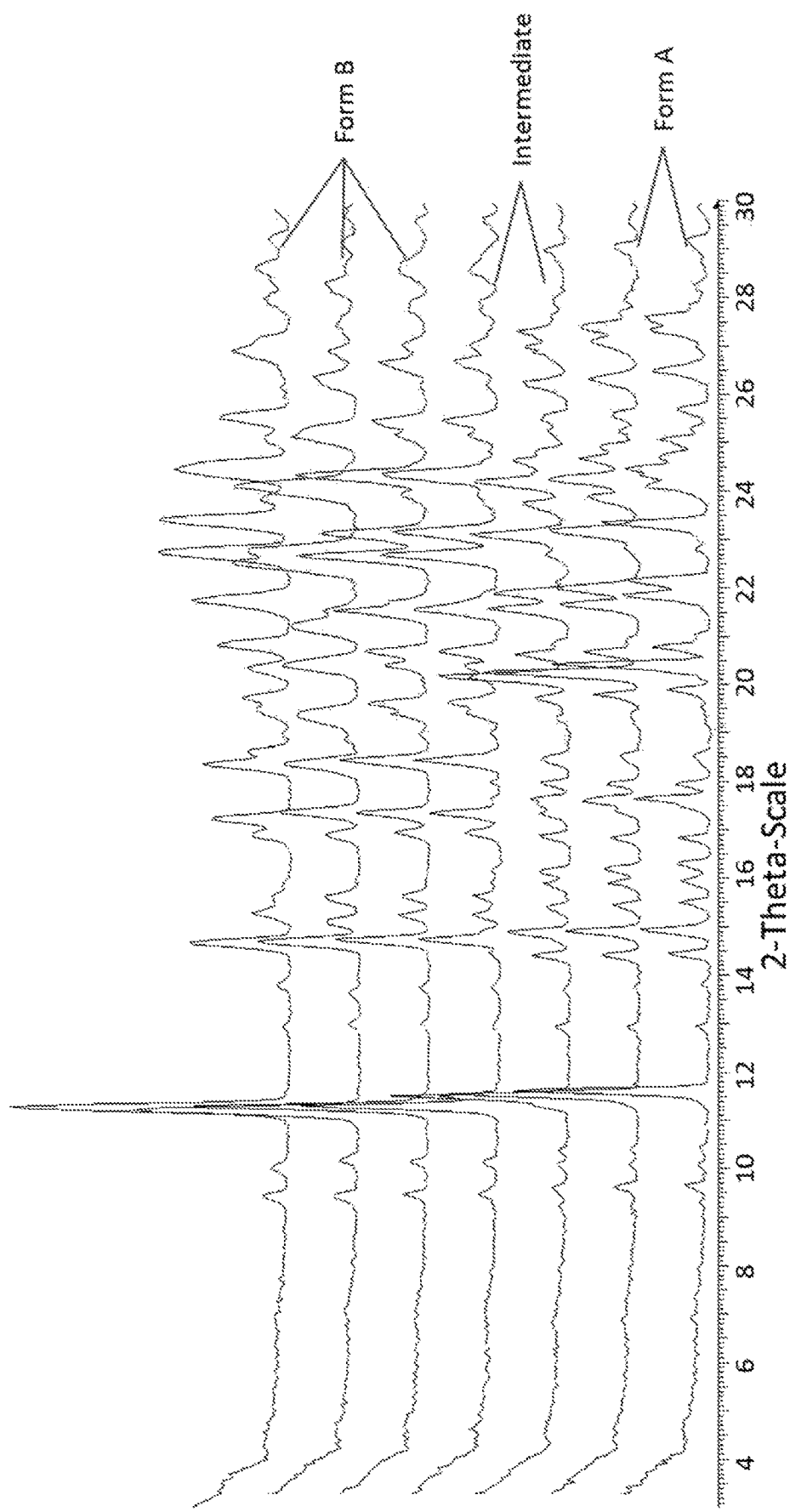
FIG. 6 is a variable temperature XRPD study of Form A 3-[5-amino-4-(3-cyanobenzoyl)-pyrazol-1-yl]-N-cyclopropyl-4-methylbenzamide, showing the transformation into Form B.
Figure 7:
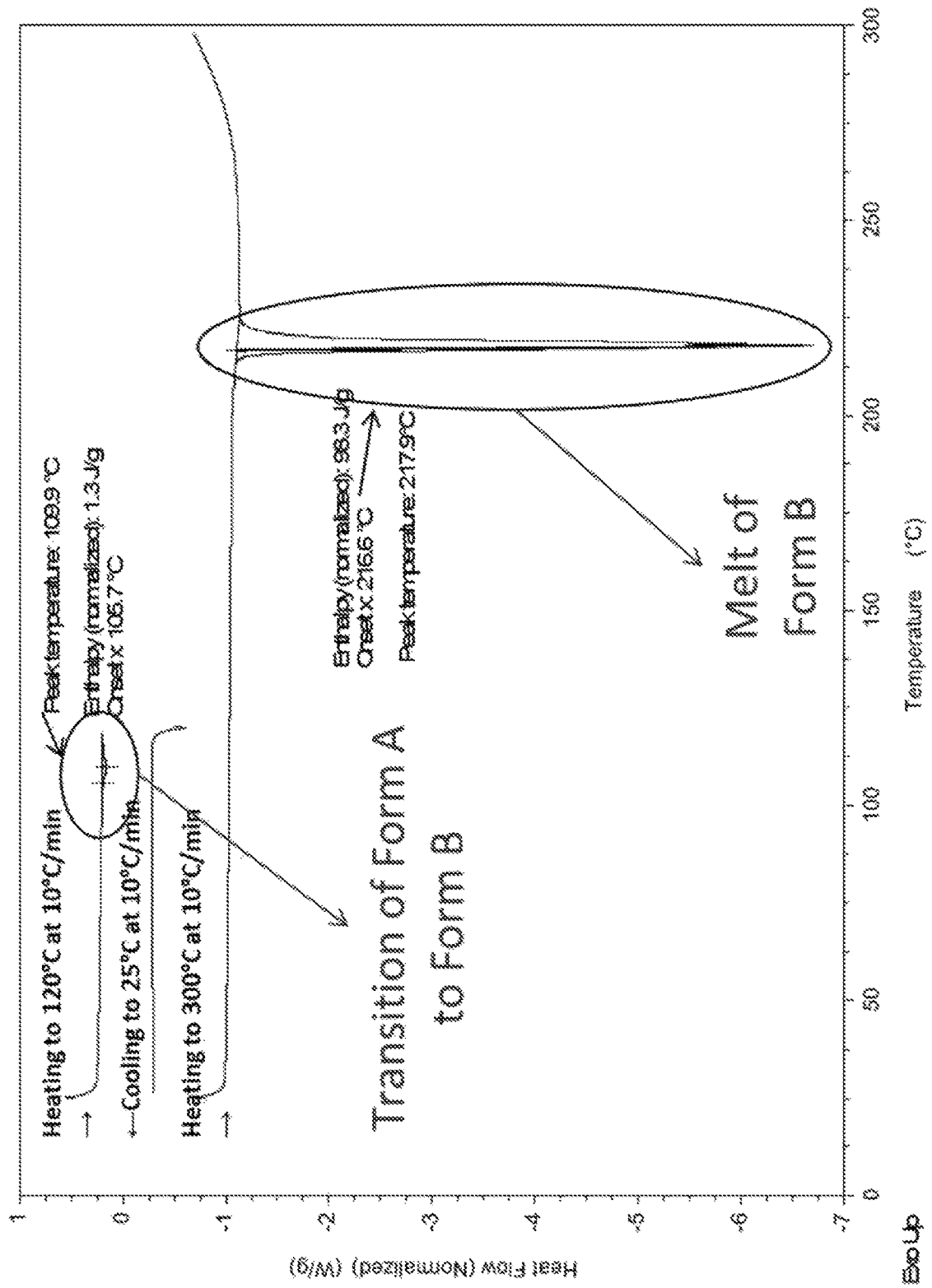
FIG. 7 shows DSC experiments performed at different heating rates (10° C./min). This shows the transition to Form B.
Figure 8:
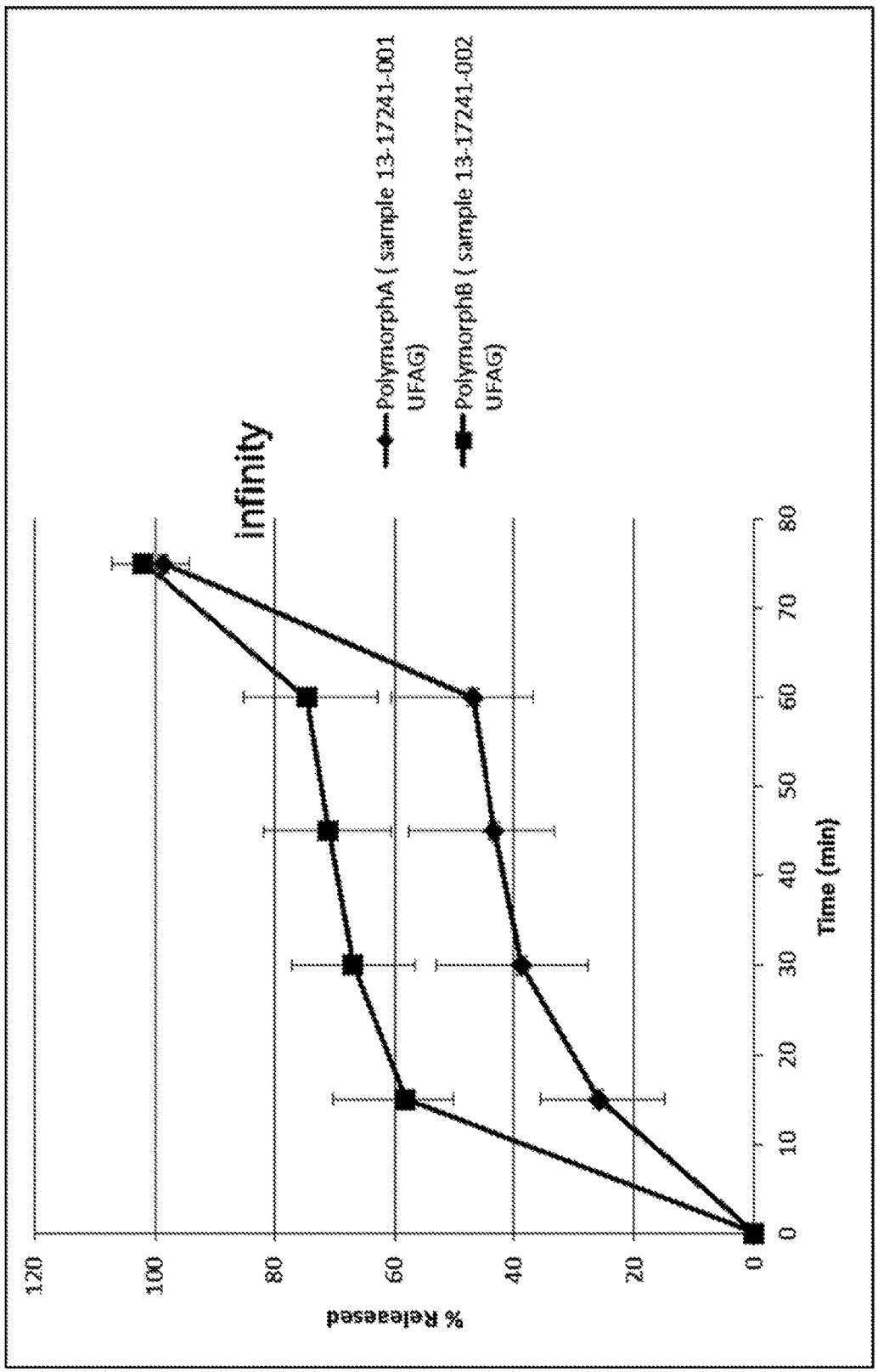
FIG. 8 shows that Form B has higher dissolution rate than Form A. It shows a comparison of Form A and Form B in size 1 capsules (50 mg drug substance/capsule). The products is milled to $D_{50}$ 1-10 µm.

The variable temperature XRPD (see FIG. 6) showed that a polymorphic form, herein designated Form A, converted to Form B on heating above 100° C. At 200° C., changes (shifts) in peak position in the high 2-theta region were observed. This may be attributed to the thermal expansion effect. However, this thermal effect was reversible and Form B remained unchanged by XRPD after cooling to room temperature (20° C.).

What is claimed is:

1. A process for the preparation of a crystalline polymorph Form B of 3-[5-amino-4-(3-cyanobenzoyl)-pyrazol-1-yl]-N-cyclopropyl-4-methylbenzamide, wherein said Form B has an X-ray powder diffraction pattern measured using Cu Kα radiation with peaks at 2θ=about 9.6, 10.1, 11.4, 13.1, 13.9, 14.8, 15.4, 15.8, 17.0, 17.4, 18.5, 18.8, 19.7, 19.9, 20.5, 21.0, 21.9, 22.9, 23.6, 24.6 and 25.7°, comprising:
    (a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution, wherein the solvent or solvents contain less than about 5 wt % of water relative to the 3-[5-amino-4-(3-cyanobenzoyl)-pyrazol-1-yl]-N-cyclopropyl-4-methylbenzamide starting material;
    (b) cooling the solution;
    (c) isolating crystals from the solution;
    (d) heating the resultant crystals to greater than 75° C. for a period of greater than 1 minute to produce Form B 3-[5-amino-4-(3-cyanobenzoyl)-pyrazol-1-yl]-N-cyclopropyl-4-methylbenzamide.

2. A process for the preparation of a crystalline polymorph Form B of 3-[5-amino-4-(3-cyanobenzoyl)-pyrazol-1-yl]-N-cyclopropyl-4-methylbenzamide, wherein said Form B has an X-ray powder diffraction pattern measured using Cu Kα radiation with peaks at 2θ=about 9.6, 10.1, 11.4, 13.1, 13.9, 14.8, 15.4, 15.8, 17.0, 17.4, 18.5, 18.8, 19.7, 19.9, 20.5, 21.0, 21.9, 22.9, 23.6, 24.6 and 25.7°, comprising:
    (a) dissolving 3-[5-amino-4-(3-cyanobenzoyl)-pyrazol-1-yl]-N-cyclopropyl-4-methylbenzamide, at a temperature of at least 40° C., in a non-aqueous solvent or mixture of non-aqueous solvents to obtain a solution;
    (b) cooling the solution;
    wherein the final temperature of process step (b) does not exceed 100° C.;
    (c) isolating crystals from the solution;
    (d) heating the resultant crystals to greater than 75° C. for a period of greater than 1 minute to produce Form B 3-[5-amino-4-(3-cyanobenzoyl)-pyrazol-1-yl]-N-cyclopropyl-4-methylbenzamide.

3. A process for the preparation of a crystalline polymorph Form B of 3-[5-amino-4-(3-cyanobenzoyl)-pyrazol-1-yl]-N-cyclopropyl-4-methylbenzamide, comprising:
    (a) dissolving 3-[5-amino-4-(3-cyanobenzoyl)-pyrazol-1-yl]-N-cyclopropyl-4-methylbenzamide, at a temperature of 90° C. or greater, in a non-aqueous solvent or mixture of non-aqueous solvents to obtain a solution;
    (b) optionally filtering the solution to substantially remove particles having a largest diameter greater than 100 μm;
    (c) cooling the solution to less than 100° C., but greater than 80° C.;
    (d) seeding the solution with Form B crystals of 3-[5-amino-4-(3-cyanobenzoyl)-pyrazol-1-yl]-N-cyclopropyl-4-methylbenzamide;
    (e) optionally cooling the solution further;
    (f) optionally further seeding of the solution with Form B crystals of 3-[5-amino-4-(3-cyanobenzoyl)-pyrazol-1-yl]-N-cyclopropyl-4-methylbenzamide;
    (g) cooling the solution to less than 70° C.
    (h) isolating the crystals of Form B 3-[5-amino-4-(3-cyanobenzoyl)-pyrazol-1-yl]-N-cyclopropyl-4-methylbenzamide.

4. The process of claim 2, wherein the temperature of process step (a) is greater than 100° C.

5. The process of claim 4, wherein the temperature of process step (d) is greater than 80° C.

6. The process of claim 5, wherein the temperature of process step (d) is maintained for greater than 5 minutes.

7. The process of claim 2, wherein the cooling in step (b) is at a cooling rate of about between 1 and 0.01° C./min.

8. The process of claim 7, wherein the nonaqueous solvent or mixture of non-aqueous solvents are selected from the group consisting of $C_{1-6}$ alcohols, $C_{4-10}$ cyclic ethers, $C_{1-6}$ nitriles, $C_{1-6}$ haloalkanes, $C_{1-6}$ ketones, dialkylformamides, dialkyl sulfoxides, $C_{3-10}$ aryls, $C_{5-10}$ alkanes, $C_{1-6}$ alkyl acetate.

9. The process of claim 8, wherein the nonaqueous solvent or solvents are selected from the group consisting of methanol, ethanol, tetrahydrofuran, acetonitrile, methylene chloride, isopropyl alcohol, acetone, N,N-dimethylformamide (DMF), dimethyl sulfoxide (DMSO), toluene, benzene, n-hexane, ethyl acetate, dichloromethane, chloroform and carbon tetrachloride.

10. The process of claim 3, wherein the solvent or solvents in step (a) contain less than about 5 wt % of water relative to the 3-[5-amino-4-(3-cyanobenzoyl)-pyrazol-1-yl]-N-cyclopropyl-4-methylbenzamide starting material.

11. The process of claim 3, wherein the temperature of the solution in step (a) is between 90° C. and 200° C.

12. The process of claim 11, wherein the filtration step (b) removes particles having a largest diameter of greater than 50 μm.

13. The process of claim 12, wherein the cooling step (c) is a temperature of greater than 85° C. and this temperature is maintained for at least 1 hour.

14. The process of claim 2, wherein during any cooling step, an anti-solvent is added, said anti-solvent being selected from $C_{1-6}$ ethers.

15. The process of claim 3, wherein the cooling step (g) is at a temperature of less than 50° C. but greater than 0° C., wherein this temperature is maintained for at least 30 minutes.

16. The process of claim 3, wherein the solvent is removed in step (h) by drying between 40-120° C., under vacuum.

17. The process of claim 3, wherein in step (g), the cool down rate is a maximum of 0.05° C./min.

18. Form B 3-[5-amino-4-(3-cyanobenzoyl)-pyrazol-1-yl]-N-cyclopropyl-4-methylbenzamide obtainable by a process of claim 2.

19. A pharmaceutical composition comprising Form B 3-[5-amino-4-(3-cyanobenzoyl)-pyrazol-1-yl]-N-cyclopropyl-4-methylbenzamide of claim 18.

Figure 2:
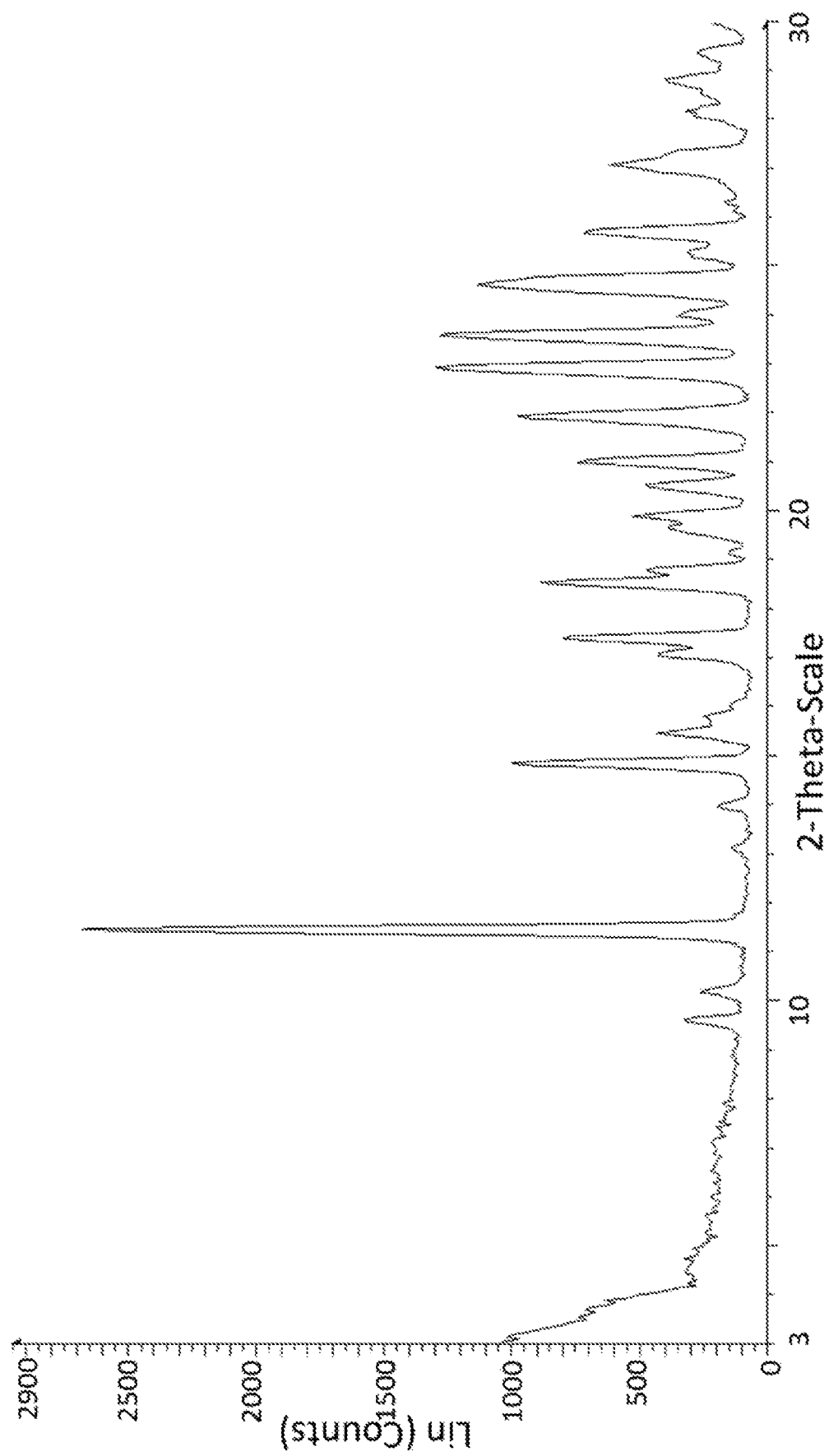
FIG. 2 is the XRPD spectrum of Form B polymorph of 3-[5-amino-4-(3-cyanobenzoyl)-pyrazol-1-yl]-N-cyclopropyl-4-methylbenzamide.
Figure 3:
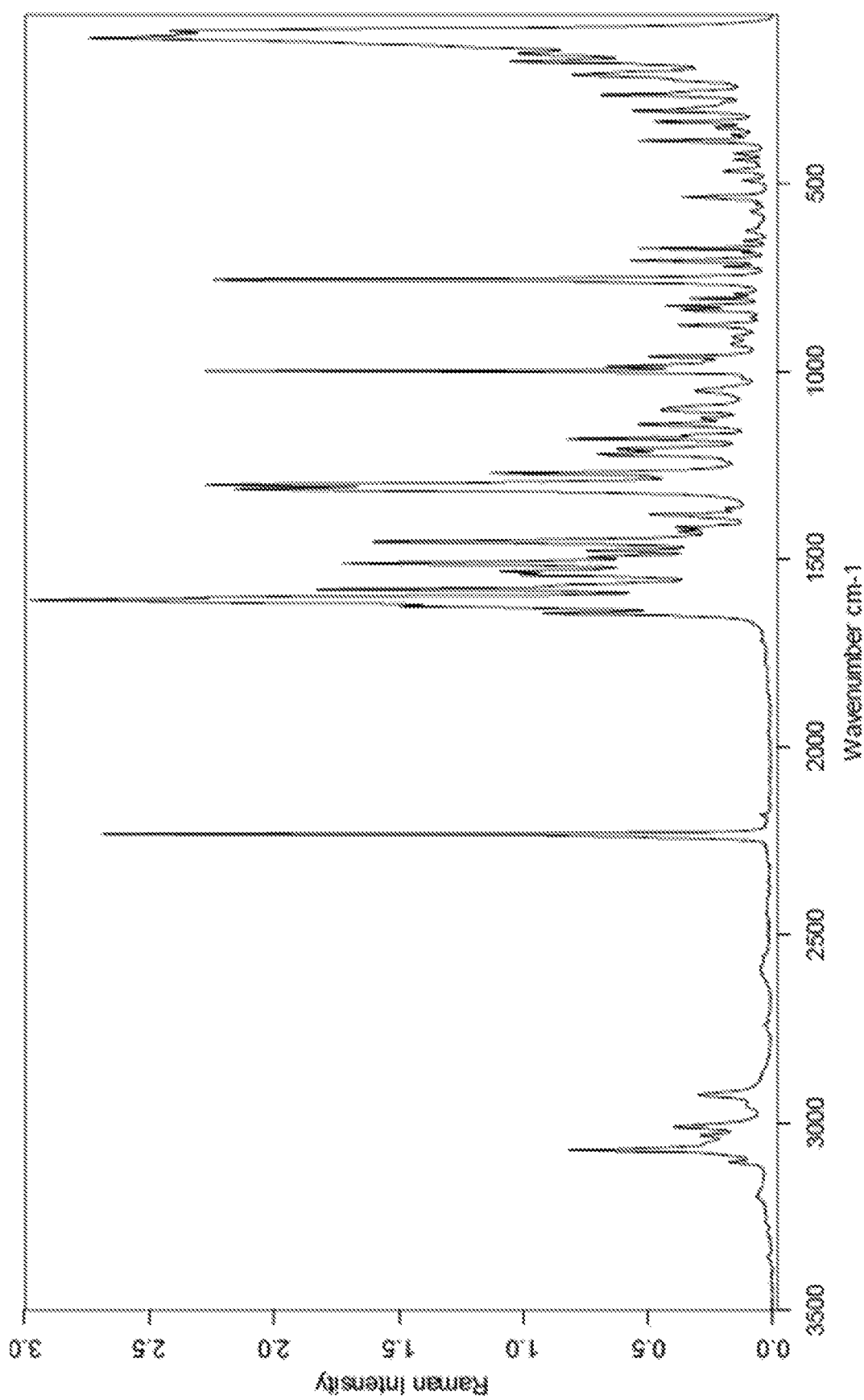
FIG. 3 is the Raman spectrum of Form B polymorph of 3-[5-amino-4-(3-cyanobenzoyl)-pyrazol-1-yl]-N-cyclopropyl-4-methylbenzamide.
Figure 4:
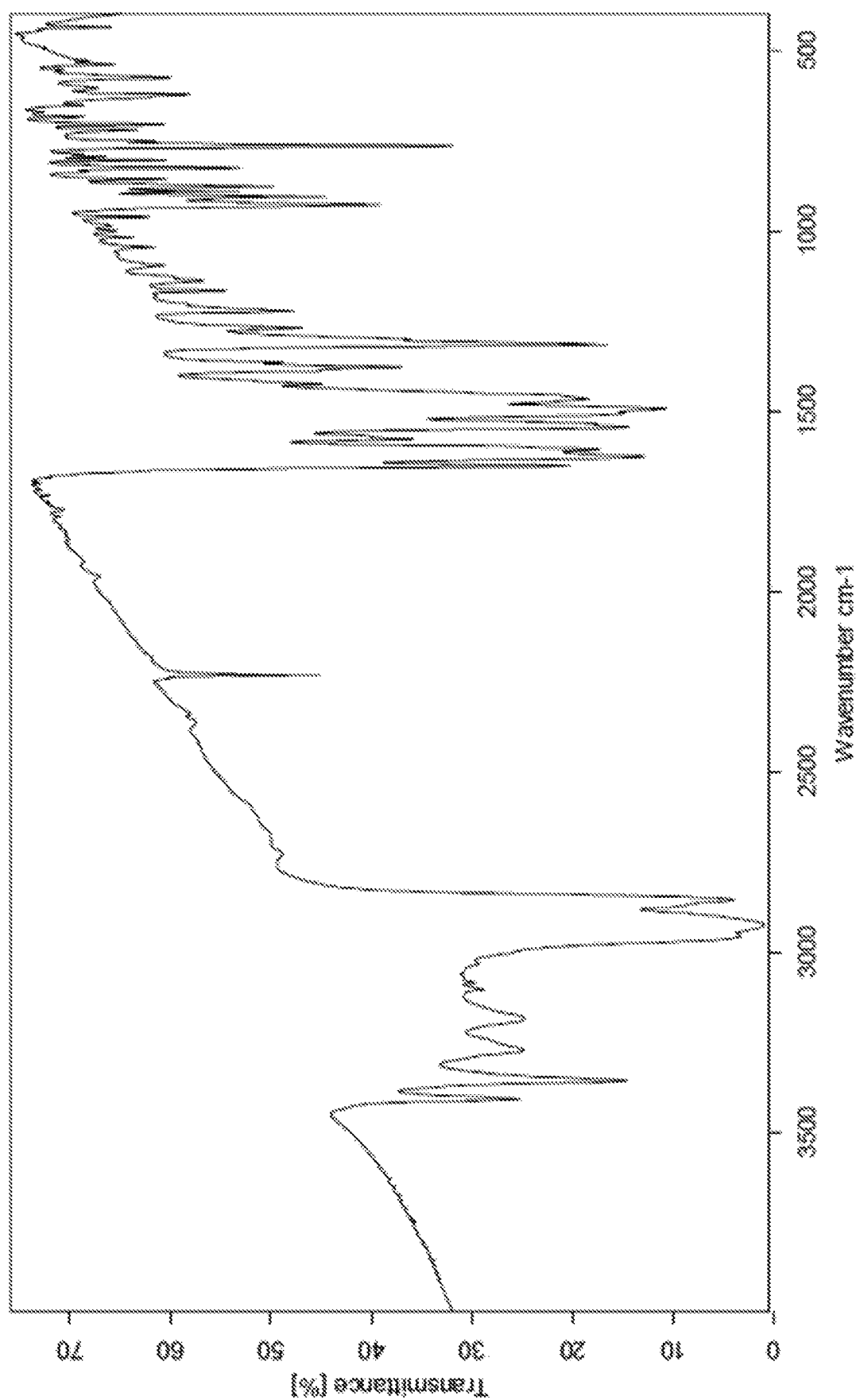
FIG. 4 is an FT-IR spectrum of Form B polymorph of 3-[5-amino-4-(3-cyanobenzoyl)-pyrazol-1-yl]N-cyclopropyl-4-methylbenzamide.

20. Form B 3-[5-amino-4-(3-cyanobenzoyl)-pyrazol-1-yl]-N-cyclopropyl-4-methylbenzamide wherein Form B exhibits an X-ray powder diffraction pattern substantially as shown in FIG. 2.

21. A pharmaceutical composition comprising Form B 3-[5-amino-4-(3-cyanobenzoyl)-pyrazol-1-yl]-N-cyclopropyl-4-methylbenzamide of claim 20.

22. Form B 3-[5-amino-4-(3-cyanobenzoyl)-pyrazol-1-yl]-N-cyclopropyl-4-methylbenzamide, wherein Form B has an X-ray powder diffraction pattern measured using Cu Kα radiation with peaks at 2θ=about 9.6, 10.1, 11.4, 13.1, 13.9, 14.8, 15.4, 15.8, 17.0, 17.4, 18.5, 18.8, 19.7, 19.9, 20.5, 21.0, 21.9, 22.9, 23.6, 24.6 and 25.7°.

23. A pharmaceutical composition comprising Form B 3-[5-amino-4-(3-cyanobenzoyl)-pyrazol-1-yl]-N-cyclopropyl-4-methylbenzamide of claim 22.

* * * * *